United States Patent [19]

Falk et al.

[11] 4,266,080

[45] May 5, 1981

[54] PERFLUOROALKYLTHIOETHYL ETHER DERIVATIVES

[75] Inventors: Robert A. Falk, New City; Karl F. Mueller, New York, both of N.Y.

[73] Assignee: Ciba-Geigy Corporation, Ardsley, N.Y.

[21] Appl. No.: 874,714

[22] Filed: Feb. 2, 1978

[51] Int. Cl.$^3$ .................... C07C 149/18; C07C 149/36
[52] U.S. Cl. ...................................... 568/45; 252/352;
260/326.5 S; 260/399; 260/402.5; 528/376;
544/158; 544/159; 544/395; 544/398; 546/184;
546/232; 546/246; 546/248; 560/32; 560/33;
560/109; 560/110; 560/111; 560/135; 560/142;
560/165; 560/222; 560/253; 560/264; 568/50;
568/51; 564/500
[58] Field of Search ......... 260/609 R, 609 F, 570.5 S,
260/584 C, 399, 402.5; 528/376; 560/142, 222,
253, 264

[56] References Cited

U.S. PATENT DOCUMENTS 3,935,277  1/1976  Dear et al. ........................ 560/222
4,001,305  1/1977  Dear et al. ........................ 260/609 R

*Primary Examiner*—Donald G. Daus
*Assistant Examiner*—M. C. Eakin
*Attorney, Agent, or Firm*—Michael W. Glynn

[57] ABSTRACT

Perfluoroalkyl compounds containing ether groups have the formula $$R_f R_1 SCH_2 CH_2 O\ T\ Z$$

wherein $R_f$ is a perfluoroalkyl, $R_1$ is alkylene or alkyleneoxy or aminoalkylene, T is alkylene, and Z is hydrogen; hydroxy; $NR_3R_4$, where $R_3$ and $R_4$ each is alkyl or together with nitrogen form a heterocyclic ring; $N^+R_3R_4(R_5)X_z^{-y}$, where $R_5$ is hydrogen, oxide, alkyl, or substituted alkyl, X is an anion, and y is 1 or 2; z is 0 or 1 or is $-OCH_2CH_2SR_1R_f$, can be prepared directly by free-radical catalyzed addition of a perfluoroalkylthiol to a vinyl ether or subsequent reaction. These compounds are useful as surfactants and oil spill collecting agents.

8 Claims, No Drawings

PERFLUOROALKYLTHIOETHYL ETHER DERIVATIVES

DETAILED DISCLOSURE

The novel perfluoroalkylthioethyl ether compounds of this invention are of the formula $$R_f R_1 SCH_2 CH_2 O\ T\ Z$$

wherein $R_f$ is straight or branched chain perfluoroalkyl of 1 to 18 carbon atoms or said perfluoroalkyl substituted by perfluoroalkoxy of 2 to 6 atoms;

$R_1$ is branched or straight chain alkylene of 1 to 12 carbon atoms; alkylenethioalkylene of 2 to 12 carbon atoms; alkylenethioalkylene of 2 to 12 carbon atoms; or alkyleneiminoalkylene of 2 to 12 carbon atoms where the imino nitrogen atom contains as a third substituent hydrogen or alkyl of 1 to 6 carbon atoms;

T is branched or straight chain alkylene of 1 to 18 carbons, or phenylene;

Z is a covalently bonded group selected from the group consisting of —H; —OCH$_2$CH$_2$SR$_1$R$_f$; —OR$_2$, where R$_2$ is hydrogen, alkyl of 1 to 25 carbon atoms, or acyl where said acyl is an aliphatic or aromatic carbonyl or carbamyl group of up to 25 carbon atoms. Thus, R$_2$ can be hydrogen alkyl of 1 to 24 carbon atoms, alkanoyl of 2 to 24 carbon atoms, alkenoyl of 3 to 24 carbon atoms, benzoyl or benzoyl substituted by 1 to 3 of chloro, bromo, alkyl of 1 to 18 carbon atoms, C$_2$–C$_{24}$ alkyl carbonate or C$_2$–C$_{24}$ alkyenylcarbamate; —NR$_3$R$_4$, where R$_3$ and R$_4$ each is independently straight or branched chain alkyl of 1 to 22 carbon atoms; or R$_3$ and R$_4$, together with the nitrogen to which they are bonded, form a piperazine, piperidine, morpholine or pyrrolidine ring; and —NR$_3$R$_4$(R$_5$)$_y$X$_z^{-y}$ where R$_5$ is hydrogen; oxide; or straight or branched chain alkyl of 1 to 22 carbon atoms which is unsubstituted or substituted with; 1 or 2 hydroxyl groups, a carboxylic acid group, or an anionic function selected from sulfonate, sulfate, or carboxylate; or R$_3$, R$_4$ and R$_5$ together with the nitrogen to which they are attached, represent pyridyl;

X is an anion; preferably selected from the group consisting of Br, Cl, I, lower alkanoate, lower alkylsulfonate, phenylsulfonate, tolysulfonate phosphate, sulfate, or lower alkylsulfate;

y is 1 or 2, depending on the valence of X; and z is zero or 1, with the proviso that when z is zero, y is 1 and R$_5$ must be oxygen or said alkyl substituted by an anionic function; if z is 1, R$_5$ may not be oxygen.

Preferred compounds are those where $R_f$ is perfluoroalkyl of 6 to 12 carbon atoms or said perfluoroalkyl substituted by perfluoroalkoxy of 2 to 6 carbon atoms;

$R_1$ is branched or straight chain alkylene of 2 to 8 carbon atoms, alkylenethioalkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the imino nitrogen atom contains hydrogen or methyl as a third substituent;

T is alkylene of 2 to 18 carbons;

Z is either:

—H or —OR$_2$, where

R$_2$ is hydrogen, alkyl of 1 to 18 carbon atoms or acyl where said acyl is an aliphatic hydrocarbon or aromatic hydrocarbon carbonyl or carbamyl group up to 18 carbon atoms, —NR$_3$R$_4$, where R$_3$ and R$_4$ each is independently straight or branched chain alkyl of 1 to 6 carbon atoms; or R$_3$ and R$_4$, together with the nitrogen to which they are bonded, form a piperazine, piperidine, morpholine or pyrrolidine ring: —NR$_3$R$_4$(R$_5$)$_y$X$_z^{-y}$, where R$_5$ is hydrogen; oxide; or straight or branched chain alkyl of 1 to 12 carbon atoms which is substituted with: 1 or 2 hydroxyl groups, carboxylic acid group, or an anionic function selected from sulfonate, sulfate, or carboxylate;

X is an anion; preferably selected from the group consisting of Br, Cl, I, acetate, phosphate, sulfate, methosulfate or ethosulfate;

y is 1 or 2, depending on the valence of X; and z is zero or 1,

Particularly preferred are those compounds where $R_f$ is perfluoroalkyl of 6 to 12 carbon atoms, $R_1$ is alkylene of 2 to 4 carbon atoms T is alkylene of 2 to 12 carbon atoms Z is —H; OR$_2$ where R$_2$ is hydrogen, alkyl of 1 to 12 carbon atoms; —NR$_3$R$_4$, where T$_3$ and R$_4$ each is independently straight chain alkyl of 1 to 2 carbon atoms; —N$^+$R$_3$R$_4$(R$_5$)$_y$X$_z^{-y}$ where R$_5$ is hydrogen, straight chain alkyl of 1 to 3 carbon atoms which is unsubstituted substituted by —COOH, or an anionic function selected from sulfonate, sulfate or carboxylate;

X is anion selected from the group consisting of Cl, I, acetate, sulfate, methosulfate and ethosulfate;

y is 1 or 2, depending on the valence of X; and z is zero or 1.

By sulfonate, sulfate and carboxylate is meant the —SO$_3^-$ and —OSO$_3^-$, and —COO$^-$ radicals, respectively.

The novel R$_f$-surfactants described herein can be obtained either;

(a) directly by the free-radical addition of a perfluoroalkylthiol of formula $$R_f R_1 SH$$

to a vinyl ether of formula $$CH_2 = CH\ O\ T\ Z$$

where R$_f$, R$_1$, T, and Z are defined above, or (b) indirectly by the further reaction of the above products wherein Z is —NR$_3$R$_4$ with such quaternizing agents as alkyl halides, dialkyl sulfates and the like to yield cationic surfactants or with inorganic acids or organic acids to form salts, or by reaction with such alkylation reagents as chloroacetic acid, sodium chloroacetate, propane sultone, propiolactone and the like, to yield amphoteric surfactants, Amine oxide derivatives wherein R$_5$ is oxygen are prepared by treatment with hydrogen peroxide at about 0° to 60° C.

(c) indirectly by the further reaction of the above products wherein Z is —OH with anhydrides or acid halides to form esters or with isocyanates to form urethanes.

One group of preferred compounds has the formula $R_fCH_2CH_2S\ CH_2CH_2OCH_2CH_2OH$ where
$R_f$ is perfluoroalkyl of 6 to 12 carbon atoms, or where
$R_f$ is perfluoroalkoxyperfluoroalkyl of 4 to 12 carbon atoms, and especially where
$R_f$ is $(CF_3)_2CFO(CF_2CF_2)_y-$ where
Y is an integer from 1 to 6.

Another group of preferred compounds have the formula
$R_fCH_2CH_2\ S\ CH_2CH_2O\ CH_2CH_2N\ (CH_3)_2$ and the corresponding ammonium derivatives
$R_fCH_2CH_2S\ CH_2CH_2O\ CH_2CH_2N^+(CH_3)_2C_2H_5\ C_2H_5SO_4^-$ and
$R_fCH_2CH_2S\ CH_2CH_2O\ CH_2CH_2N(CH_3)_2N^+(CH_3)_2CH_2CO_2^-$ where $R_f$ is as described above.

In one embodiment the vinyl ether has the formula $CH_2=CHO-T-OH$ where T is a straight chain alkylene of 2 to 4 carbon atoms.

In another embodiment the vinyl ether has the formula $CH_2=CHO-T-NR_3R_4$ where T is a straght chain alkylene of 2 to 3 carbon atoms, and $R_3$ and $R_4$ are each independently straight chain alkyl of 1 to 3 carbon atoms; or $R_3$ and $R_4$ are both methyl or ethyl groups.

The vinyl ethers which are generally available and are particularly useful for this invention include:
isooctyl vinyl ether
decyl vinyl ether
hexadecyl vinyl ether
octadecyl vinyl ether
butanediol divinyl ether
diethylene glycol divinyl ether
dimethylaminoethyl vinyl ether
hydroxybutyl vinyl ether
2-methoxyethyl vinyl ether
2-hydroxyethyl vinyl ether
phenyl vinyl ether Perfluoroalkyl thiols useful herein are well documented in the prior art. For example, thiols of the formula $R_fR'-SH$ have been described in a number of U.S. Patents including U.S. Pat. Nos. 2,894,991; 2,961,470; 2,965,677; 3,088,849; 3,172,190; 3,544,663; and 3,655,732.

Thus, U.S. Pat. No. 3,655,732 discloses mercaptans of formula $R_f-R'-SH$ where R' is alkylene of 1 to 16 carbon atoms and $R_f$ is perfluoroalkyl and teaches that halides of formula $R_f-R'hal$ are well known. Reaction $R_fI$ with ethylene under free-radical conditions gives $R_f(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $R_f-R'-X-R''-SH$ where R' and R'' are alkylene of 1 to 16 carbon atoms, with the sum of carbon atoms of R' and R'' being no greater than 25; $R_f$ is perfluoroalkyl of 4 through 14 carbon atoms and X is $-S-$ or $-NR'''$ where R''' is hydrogen or alkyl of 1 through 4 carbon atoms.

U.S. Pat. No. 3,544,663 teaches that the mercaptan $R_fC_2CH_2SH$ where $R_f$ is perfluoroalkyl of 5 to 13 carbon atoms, can be prepared by reacting the perfluoroalkylalkylene iodine with thiourea or by adding $H_2S$ to a perfluoroalkyl substituted ethylene $(R_f-CH=CH_2)$, which in turn can be prepared by dehydrohalogenation of the halide $R_f-CH_2CH_2-hal$.

The reaction of the iodide $R_f-R'-I$ with thiourea followed by hydrolysis to obtain the mercaptan $R_f-R'-SH$ is the preferred synthetic route. The reaction is applicable to both linear and branched chain iodides. U.S. Pat. No. 3,514,487 described perfluoroalkoxyalkyl iodides of general formula $(CF_3)_2CFOCF_2CF_2(CH_2CH_2)_mI$ where m is 1-3.

Particularly preferred herein are the thiols of formula $R_fCH_2CH_2SH$ where $R_f$ is perfluoroalkyl of 6 to 12 carbon atoms. These $R_f$-thiols can be prepared from $R_fCH_2CH_2I$ and thiourea in very high yields.

For the addition of a perfluoroalkylthiol of formula $R_fR_1SH$ to a vinyl ether it is necessary to use an azo-type free-radical catalyst.

The reaction temperature and choice of azo-type free-radical catalyst are considered to be mutually dependent. The temperature range of 40° C. to 100° C. is one wherein the formation of undesirable by-products is minimized and wherein the reaction products are stable. In order to achieve a reasonable reaction rate of these temperatures, it is desirable to use an azo-type catalyst that is reactive to a reasonable extent in this temperature range. It is, therefore, preferred to use an azo-type free-radical catalyst having a 1-hour half-life temperature of 40° to about 100° C.

Suitable solvents are such in which the reactants are soluble at reaction temperatures and include aliphatic or aromatic hydrocarbons such as heptane, benzene, toluene, etc; chlorinated or fluorinated aliphatic or aromatic hydrocarbons such as methylene chloride, chloroform, methyl chloroform, carbon tetrachloride, trichloroethylene, perchloroethylene, Freon's such as 1,1,2-trifluoro-1.2.2-trichloroethane, etc., chlorobenzene, benzotrifluoride or hexafluoroxylene, ketones, esters and ethers such as acetone, methyl isobutyl ketone, ethyl acetate and higher homologs, dialkyl ethers, tetrahydrofuran, ethylene glycol monomethyl or monoethyl ether, ethylene glycol dimethyl or diethyl ether, and acetonitrile.

If possible it is preferred to carry out the addition reaction in bulk.

Vinyl ethers are described in "Acetylene—Its Properties, Manufacture and Uses," Vol. 2, E. Bern Ltd, London and in brochures of the GAF Corporation.

The novel surfactants of this invention are useful to improve or impart properties such as:
wetting, penetration, spreading, leveling, foam stability, flow properties, emulsification, dispersion, and oil and water repellency. Based on these unique properties are numerous applications, some of which follow. Although applications are suggested for a particular use area, the general applicability of each concept is inferred for other applications.

PLASTICS AND RUBBER INDUSTRY

Emulsifying agent for polymerization, particularly fluoromonomers
As a latex stabilizer
To aid in the preparation of agglomerates of powdered fluorocarbon polymers.

In synergistic mixtures with hydrocarbon surfactants to wet low energy surfaces including natural and synthetic rubbers, resins, plastics
As an adjuvant for foam applications and as foaming agents to aid in leak detection.
As a foam additive to control spreading, crawling, edge build up.
As mould release agents, for silicones, etc.
In refractory processes
As an anti-mist film former
Additive for elimination of trapped air in plastic laminates
Wetting agent for resin molds for definition, strength
Hot-melt additive for oil and grease repellency
Resin additive for improved wetting of and bonding with fillers
Flow modifier for extruding hot melts; spreading, uniformity, anticratering
Adjuvant for resin etchant
Mold release agent, demoulding agent
Retarder for plasticizer migration or evaporation
Internal antistatic agent for polyolefins
Antiblocking agent of polyolefins

PETROLEUM INDUSTRY

Wetting assistant for oil well treatments, drilling muds
As a film evaporation inhibitor for gasoline, jet fuel, solvents, hydrocarbons
Lubricating, cutting oil improver, to improve penetration times
In extreme pressure EP lubricants
Oil spill collecting agent
Additive to improve tertiary oil recovery

TEXTILE AND LEATHER INDUSTRIES

Soil release and soil proofing agent
Oil/water repellent textile and leather treatment
Wetting agent to improve coverage and penetration of pores of substrates
Anti-foaming agent in textile treatment baths
Wetting agent for finish-on-yarn uniformity
Penetrating agent for finishes on tow, heavy denier fibers
Emulsifying agent/lubricant/for fiber finishes
Cleaner/metal treating agent for polymerization equipment
Flow modifier for spinning of hot melts, solutions
Additive for fabric finishes for spreading, uniformity
Wetting agent for dyeing
Penetration aid for bleaches
Wetting agent for binder in nonwoven fabrics

PAINT, PIGMENT AND FINISHING INDUSTRIES

Leveling, anti-cratering adjuvant for finishes and paint
Adjuvant for control of soiling
Agent to control differential evaporation of solvents
Leveling agent for floor waxes
Adjuvant for waxes to improve oil and water repellency
Adhesion improver for oily or greasy surfaces
To combat pigment flotation problems
Improver for automotive finishes, based on water-based coatings in which the pigments are rendered non-reactive
Pigment grinding aid to promote wetting, dispersion, color development
Foam generator substance for the application of dyes, inks
Electrolytic conversion coatings

MINING AND METALWORKING INDUSTRIES

In cleaning agents for property improvement
Additive for solvent cleaning
Additive for metal pickling baths to increase bath life and acid runoff
Additive for chrome electroplating: surface tension reduction, foaming
Additive for soldering flux, especially for electronic circuitry
Protective agent for coatings (tarnish resistance, grease repellency)
Corrosion inhibitor
Additive for etchant solution for improved definition
To form antimist films and anti-condensation surfaces
Plastic preplate and silicon etchant technology
In soldering flux for microelectronics to reduce foaming
In chemical roughing agent solutions, prior to galvanization
As a colloidal dispersion aid for magnetic solids
Protective coatings for aluminum and as an antiblocking agent
Wetting agent for leaching copper ores and as a froth flotation agent
To promote ore wetting and quicker breaking of the protective oxide layer

PHARMACEUTICAL INDUSTRY

Improve the properties and penetration of antimicrobial agents
Improve the properties of biochemicals, biocides, algicides, bacteriocides, and bacteriostats
Improve the strength, homogeneity, and reduce the permeability of encapsulated materials
Emulsify fluorochemical blood substitutes

AGRICULTURE AND FORESTRY

Wetting agent for herbicides, fungicides, weed killers, hormone growth regulators, parasiticides, insecticides, germicides, bactericides, nematocides, microbiocides, defolients and fertilizers
As an ingredient in chemosterilents, insect repellents and toxicants
For wettable powder pesticides and chemical powders
Corrosion inhibitor for chemical applicators
Wetting agent for foliage
Wetting additive for live stock dips, or to wet sheep skins during desalination
Wetting adjuvant for manufacture of plywood veneer
Penetrant for preservative impregnation
Pulping aid
For cleaning tubes in paper making dyeing
Grease/oil repellents for paper

FIRE FIGHTING

Wetting agent for fighting forest fires
Ingredient of AFFF, aqueous film forming extinguishing agents
Component of fluoroprotein foams
Additives to dry chemical extinguishing agents
Agent in aerosol-type extinguishers Wetting agent for sprinkler water

AUTOMOTIVE, BUILDING MAINTENANCE AND CLEANING

Wetting agent for cleaning compositions
Additive for alkaline cleaners
Glass cleaner
Wetting agent for automobile waxes
Adjuvant to improve oil/water repellency of wax
Lubricant/corrosion inhibitor for antifreeze
Rinse-aid for car washes
In dry cleaning compositions and solvent cleaners, for water displacement and foaming. May improve soil suspension and decrease redeposition
Foaming agents for pipe cleaning
Anti-mist film former for glass and plastics
In foams for dust suppresion
Cleaner for building exteriors
For acidic concrete cleaners
Air entrainment additive for low density concrete
Bubble former for air tracing, in ventilating systems

HOUSEHOLD, COSMETIC AND PERSONAL PRODUCTS

Rinse-aid for dishwashing
Liquid polishing compositions
Floor polish leveling agent
Additive for alkaline oven cleaners
Synergistic improver for disinfectants
Carpet cleaners
Synergistic wetting agent in detergent formulations
Additive for protective coatings on metals (tarnish resistance, grease resistance)
Gloss and antistatic improver
Hair shampoo ingredient
Shaving foam ingredient
Oil and water repellent cosmetic powders ingredient
Ingredient of lotions or creams for skin or hair
Ingredient of skin protection creams

PHOTOGRAPHY AND GRAPHIC ARTS

Printing ink additive for ink flow and leveling, both aqueous and solvent based.
Wetting agent for writing inks
To combat pigment flooding and flotation in printing inks
To form ink repellent surfaces for waterless lithoplates, or electrographic coatings.
Prevent reticulation of gelatin layers and improve uniformity
Assist in film drying
Improve film coatings and reduce "contraction flecks"
Wetting, leveling, anti-cratering assist agent
Surfactant for developer solutions
Photoemulsion stabilizer
Prevent photo-lubricant agglomeration
Coating aid in the preparation of multiple layer film elements
Antistatic wetting agent for film coatings
Antifogging agent for films
Bonding agent for fillers and fluoropolymer films
In coatings for nematic liquid crystal cells The following examples are presented to illustrate the preparation of the novel compounds of this invention and to demonstrate their valuable surface properties and utility as oil spill collecting agents.

EXAMPLE 1

2-(1,1,2,2-Tetrahydroperfluorodecanethio)ethyl hydroxyethyl ether

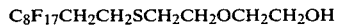
$C_8F_{17}CH_2CH_2SCH_2CH_2OCH_2CH_2OH$ 1,1,2,2-Tetrahydroperfluorodecanethiol (4.82 g, 0.0100 mole), 2-hydroxyethyl vinyl ether (0.93 g, 0.0105 mole), and 2,2'-azobis(2-methylpropionitrile) (0.03 g) were reacted in methanol (3.5 g) at 60° C. overnight. The product was distilled at 121° C. under diffusion vacuum pump to yield 5.23 g product (92.1% of theory) as a white solid which was 100% pure by GLC. NMR showed proton resonances at 1.80, 1 proton, O$\underline{H}$ 2.00–2.60, 2 protons, CF$_2$C$\underline{H}_2$CH$_2$S; 2.80, 4 protons, CF$_2$CH$_2$C$\underline{H}_2$SCH$_2$CH$_2$O; and 3.70, 6 protons, SCH$_2$C$\underline{H}_2$OCH$_2$CH$_2$OH. Analysis for $C_{14}H_{13}F_{17}O_2S$: Calc.: C, 29.59; H, 2.31; F, 56.83. Found: C, 29.35; H, 2.28 F, 56.19.

EXAMPLE 2

2-(1,1,2,2-Tetrahydroperfluorododecanethio)ethyl hydroxyethyl ether $C_{10}F_{21}CH_2CH_2SCH_2CH_2OCH_2CH_2OH$ 1,1,2,2-Tetrahydroperfluorododecanthiol (11.60 g., 0.02 mole), 2-hydroxyethyl vinyl ether (1.76 g., 0.02 mole), and 2,2'-azobis(2-methylpropionitrile) (0.05 g.) were reacted in methanol (10 ml) at 60° C. overnight. The product was distilled at 135° C. under diffusion vacuum pump to yield 12.1 g (90.5% of theory) as a waxy white solid which was 96.0% pure by GLC. The melting point range was 93.0° to 96.0°.

Analysis for $C_{16}H_{13}F_{21}O_2S$: Calc.: C, 28.76; H, 1.96; F, 59.70. Found: C, 28.60; H, 1.88 F, 59.09.

EXAMPLE 3

2-(1,1,2,2-Tetrahydroperfluorodecanethio)ethyl 4-hydroxybutyl ether

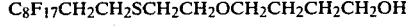
$C_8F_{17}CH_2CH_2SCH_2CH_2OCH_2CH_2CH_2CH_2OH$ 1,1,2,2-Tetrahydroperfluorodecanethiol (4.82 g, 0.0100 mole), 4-hydroxybutyl vinyl ether (1.22 g, 0.0105 mole), and 2,2'-azobis(2-methylpropionitrile) (0.03 g) were reacted in methanol (3.5 g) at 60° C. overnight. The product was distilled at 132° C. under diffusion vacuum pump to yield 4.19 g product (70.3% of theory) as a white solid which was 100% pure by GLC. NMR showed proton resonances at δ1.65, 4 protons, OCH$_2$C$\underline{H}_2$C$\underline{H}_2$OH.

Analysis for $C_{16}H_{17}F_{17}O_2S$: Calc.: C, 32.22; H, 2.87; F, 54.16. Found: C, 32.18; H, 2.87; F, 54.03.

EXAMPLE 4

2-(1,1,2,2-Tetrahydroperfluorodecanethio)ethyl 4-hydroxybutyl ether

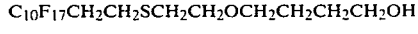
$C_{10}F_{17}CH_2CH_2SCH_2CH_2OCH_2CH_2CH_2CH_2OH$ 1,1,2,2-Tetrahydroperfluorodecanethiol (11.60 g., 0.02 mole), 4-hydroxybutyl vinyl ether (2.32 g., 0.02 mole) and 2,2'-azobis-(2-methylpropionitrile) (0.05 g.) were reacted in methanol (10 ml) at 60° C. overnight. The product was crystallized from methanol and distilled at 147° C. under diffusion vacuum pump to yield 5.65 g.

(40.6% of theory) as a waxy white solid which was 97.2% pure by GLC. The melting point range was 86.0° to 87.2° C.

Analysis for $C_{18}H_{17}F_{21}O_2S$: Calc.: C, 31.05; H, 2.46; F, 57.29. Found: C, 30.88; H, 2.62; F, 56.44.

EXAMPLE 5

2-(1,1,2,2-Tetrahydroperfluorodecanethio)ethyl 4-hydroxybutyl ether

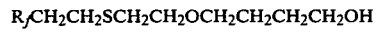

1,1,2,2-Tetrahydroperfluorodecanethiol (10.00 g, 0.0229 mole), 4-hydroxybutyl vinyl ether (2.55 g, 0.0250 mole), and 2,2'-azobis-(2-methylpropionitrile) (0.05 g) were reacted at 60° C. overnight. The resultant mixture was stripped of all non-product volatiles to yield 11.2 g product as a water white liquid (92.4% of theory) which was 98.9% pure by GLC. NMR showed proton resonances at δ1.02, 4 protons, OCH$_2$CH$_2$CH$_2$CH$_2$OH: δ2.00–2.60, 2 protons, CH$_2$CH$_2$CH$_2$; δ2.23, 1 proton; CH$_2$OH; δ2.76–2.83, 4 protons, CH$_2$SCH$_2$; δ3.54–3.67, 6 protons, CH$_2$OCH$_2$CH$_2$CH$_2$OH.

EXAMPLE 6

2-Dimethylaminoethyl 2'-(1,1,2,2-tetrahydroperfluorodecanethio) ethyl ether

C$_8$F$_{17}$CH$_2$CH$_2$SCH$_2$CH$_2$OCH$_2$CH$_2$N(CH$_3$)$_2$ 1,1,2,2-Tetrahydroperfluorodecanethiol (15.00 g, 0.031 mole), dimethylaminoethyl vinyl ether (3.78 g, 0.033 mole), and 2,2'-azobis-(2-methylpropionitrile) (0.10 g) were reacted at 70° C. for 5 hours. The resultant mixture was stripped of volatiles and distilled at 110° C./0.02 mm Hg to yield 15.95 g of light yellow liquid (85.9% of theory) which was 99.6% pure by GLC. NMR showed proton resonances at δ2.16, 6 protons, 2×CH$_2$NCH$_3$; δ2.20–2.84, 8 protons, CH$_2$CH$_2$CH$_2$SCH$_2$CH$_2$OCH$_2$CH$_2$N(CH$_3$)$_2$; δ3.40–3.74, 4 protons, 2×0 CH$_2$.

Analysis for $C_{16}H_{18}F_{17}NOS$: Calc.: C, 32.28; H, 3.05; F, 54.25; N, 2.35. Found: C, 32.16; H, 2.83; F, 54.26; N, 2.17.

EXAMPLE 7

2-(1,1,2,2-Tetrahydroperfluorodecanethioethoxy)ethyltrimethylammonium iodide

C$_8$F$_{17}$CH$_2$CH$_2$SCH$_2$CH$_2$OCH$_2$CH$_2$N$^+$(CH$_3$)$_3$ $^-$I

2-Dimethylaminoethyl 2'(1,1,2,2-tetrahydroperfluorodecanethio) ethyl ether (4.76 g, 0.008 mole), iodomethane (2.27 g, 0.016 mole), and methanol (3 g) were reacted overnight at room temperature. The product was crystallized twice from methanol to yield 4.15 g of white powder (70.3% of theory). NMR showed proton resonances at δ2.58, 2 protons, C$_8$F$_{17}$CH$_2$; δ2.82, 4 protons, CH$_2$SCH$_2$; δ3.15, 9 protons, 3×N$^+$CH$_3$; δ3.60–3.67, 4 protons, SCH$_2$CH$_2$OCH$_2$CH$_2$N$^+$; δ3.89, 2 protons, OCH$_2$CH$_2$$^+$N.

Analysis for $C_{17}H_{21}F_{17}NOS$: Calc.: C, 27.69; H, 2.87; F, 43.80; I, 17.21; N, 1.90. Found: C, 27.57; H, 2.67; F, 44.56; I, 16.92; N, 1.93.

EXAMPLE 8

2-(1,1,2,2-Tetrahydroperfluorodecanethioethoxy)ethyldimethylammonium ethyl sulfate

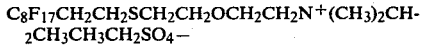

2-Dimethylaminoethyl 2'(1,1,2,2-tetrahydroperfluorodecanethio) ethyl ether (2.02 g, 0.0034 mole), and diethyl sulfate (0.54 g, 0.0035 mole) were reacted in methanol (4.00 g) overnight at 40° C. All volatiles were stripped off under high vacuum to give 2.05 g product (80.4% of theory) as a yellow gel NMR showed proton resonances at δ1.20, 6 protons, NCH$_2$CH$_3$ and CH$_3$CH$_2$SO$_4$; δ2.21, 4 protons, CH$_2$SCH$_2$; δ2.50, 2 protons, C$_8$F$_{17}$CH$_2$; δ3.06–3.40, 6 protons, CH$_3$NCH$_3$, δ3.26–3.98, 8 protons, CH$_2$OCH$_2$ and CH$_2$NCH$_2$.

Analysis for $C_{20}H_{28}F_{17}NO_5S_2$: Calc.: C, 32.05; H, 3.77; F, 43.09; N, 1.87. Found: C, 29.47; H, 3.36; F, 44.46; N, 1.81.

EXAMPLE 9

2-Dimethylaminoethyl 2'-(1,1,2,2-tetrahydroperfluoroalkylthio) ethyl ether

1,1,2,2-Tetrahydroperfluoroalkenethiol (14.00 g, 0.032 mole), dimethylaminoethyl vinyl ether (3.78 g, 0.033 mole), and 2,2'-, azobis(2-methylpropionitrile) (0.10 g) were reacted under nitrogen at 70° C. for 5 hours. The resultant amber colored liquid was 98.3% pure by GLC.

EXAMPLE 10

2-(1,1,2,2-Tetrahydroperfluoroalkylthioethoxy)ethyltrimethylammonium iodide

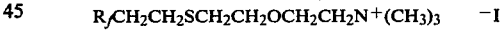

2-Dimethylaminoethyl 2'-(1,1,2,2-tetrahydroperfluoroalkylthio) ethyl ether (500 g 0.009 mole), iodomethane (2.52 g, 0.018 mole), and methanol (3.00 g) were combined resulting in a mild exotherm and allowed to set at room temperature for 3 hours. The resultant mixture was dried at 100° C./0.02 mm Hg and ground up to yield 5.70 g product (90.9% of theory) as a yellow solid.

Analysis for fluorine: Calc.: F, 41.29. Found: F, 42.56.

The following perfluoroalkylthioethyl ethers and derivatives can be prepared by procedures similar to those given on Examples 1–10.

EXAMPLES 11–22

| R$_f$thiol | Vinyl Ether | Further Reaction With |
|---|---|---|
| 11. (CF$_3$)$_2$CFOCF$_2$CH$_2$CH$_2$CH$_2$SH | CH$_2$=CHOCH$_3$ | None |
| 12. (CF$_3$)$_2$CFOCF$_2$CH$_2$CH$_2$CH$_2$SH | CH$_2$=CHOC$_{16}$H$_{33}$ | None |
| 13. C$_6$F$_{13}$CH$_2$CH$_2$SH | CH$_2$=CHOCH$_2$CH$_2$OH | None |
| 14. C$_6$F$_{13}$CH$_2$CH$_2$SH | CH$_2$=CHOCH$_2$CH$_2$N(CH$_3$)$_2$ | None |
| 15. CF$_3$CF$_2$CH$_2$SH | CH$_2$=CHOCH$_2$CH$_2$N(CH$_3$)$_2$ | CH$_3$I |
| 16. CF$_3$CF$_2$CH$_2$SH | CH$_2$=CHOCH$_2$CH$_2$N(C$_2$H$_5$)$_2$ | 1,3- |

EXAMPLES 11-22-continued

| | $R_f$thiol | Vinyl Ether | Further Reaction With |
|---|---|---|---|
| 17. | $C_8F_{17}(CH_2)_4SH$ | $CH_2=CHOC_6H_5$ | propane sultone |
| 18. | $C_8F_{17}(CH_2)_4SH$ | $CH_2=CHOC_2H_4OCH=CH_2$ | None |
| 19. | $C_8F_{17}CH_2CH_2OCH_2CH_2CH_2SH$ | $CH_2=CHO(CH_2)_4OH$ | None |
| 20. | $C_8F_{17}CH_2CH_2OCH_2CH_2CH_2SH$ | $CH_2=CHO(CH_2)_4OH$ | $C_6H_5N=C=O$ |
| 21. | $C_8F_{17}CH_2CH_2N(CH_3)CH_2CH_2CH_2SH$ | $CH_2=CHO(CH_2)_2OH$ | $CH_3COCl$ |
| 22. | $C_8F_{17}CH_2CH_2N(CH_3)CH_2CH_2CH_2SH$ | $CH_2=CHO(CH_2)_2OH$ | $(CH_3CO)_2O$ |
| 23. | $R_fCH_2CH_2SH$ | $CH_2=CHO(CH_2)_2OH$ | None |

Oil Spill Collecting Examples of Selected Examples

The subject fluorochemicals have special utility as oil spill collecting agents, as described in a copending application. Preferred candidates are low viscosity fluids which form insoluble monolayers with high spreading pressures, and have a persistent oil film clearing ability and durability.

| Example | State | Maximum Spreading Pressure ,dynes/cm | Clearing Durability |
|---|---|---|---|
| 5 | liquid | 57 | excellent |
| 23 | liquid | 56 | excellent |
| 1 | solid | 57 (in solvent) | — |
| 3 | solid | 57 (in solvent) | — |
| 2 | solid | insoluble | — |
| 4 | solid | 54 (in solvent) | — |

Surface Properties of Selected Examples

| | Surface Concentration at Concentration | | | |
|---|---|---|---|---|
| Example | 0.1% | 0.01% | 0.001% | 0.00% |
| 7 | 20.8 | 31.5 | 43.2 | |
| 10$^a$ | | 24.8 | 42.7 | 57.3 |
| 10$^b$ | | 24.5 | 45.5 | 54.6 |

$^a R_f$-distribution $C_6,C_8,C_{10},C_{12}$-40,40,13,2
$^b R_f$-distribution $C_6,C_6,C_{10},C_{12}$-32,36,22,6

I claim:
1. A perfluoroalkylthioethylether of the formula

$R_fR_1SCH_2CH_2OTZ$ wherein
$R_f$ is straight or branched chain perfluoroalkyl of 1 to 18 carbon atoms, or said perfluoroalkyl substituted by perfluoroalkoxy of 2 to 6 carbon atoms;
$R_1$ is straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent hydrogen or alkyl of 1 to 6 carbon atoms;
T is straight or branched chain alkylene of 1 to 18 carbon atoms or phenylene; and
Z is —H or —$OR_2$
where $R_2$ is hydrogen, alkyl of 1 to 24 carbon atoms, alkanoyl of 2 to 24 carbon atoms, alkenoyl of 3 to 24 carbon atoms.

2. A compound according to claim 1, wherein $R_f$ is perfluoroalkyl of 6 to 12 carbon atoms, $R_1$ is alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms wherein the imino nitrogen contains hydrogen or methyl as the third substituent;
T is alkylene of 2 to 18 carbon atoms; and
Z is H or —$OR_2$ where $R_2$ is hydrogen, alkyl of 1 to 18 carbon atoms, alkanoyl of 2 to 24 carbon atoms, alkenoyl of 3 to 24 carbon atoms.

3. A compound according to claim 1, wherein $R_f$ is perfluoroalkyl of 6 to 12 carbon atoms; $R_1$ is alkylene of 2 to 4 carbon atoms; T is alkylene of 2 to 12 carbon atoms; and Z is —$OR_2$ wherein $R_2$ is hydrogen or alkyl of 1 to 12 carbons.

4. A compound according to claim 1 of the formula $R_fCH_2CH_2SCH_2CH_2OCH_2CH_2OH$ wherein
$R_f$ is perfluoroalkyl of 6 to 12 carbon atoms, or perfluoroalkoxyperfluoroalkyl of 4 to 12 carbon atoms.

5. A compound according to claim 1 wherein Z is —H.

6. A compound according to claim 1, wherein Z is —$OR_2$.

7. A compound according to claim 2, wherein Z is —H.

8. A compound according to claim 2, wherein Z is —$OR_2$.

* * * * *